(12) United States Patent
Paul et al.

(10) Patent No.: US 10,010,399 B2
(45) Date of Patent: Jul. 3, 2018

(54) LOW PROFILE INTRALUMINAL FILTERS

(71) Applicant: Cook Medical Technologies LLC, Bloomington, IN (US)

(72) Inventors: Ram H. Paul, Bloomington, IN (US); Charles W. Agnew, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 285 days.

(21) Appl. No.: 14/839,279

(22) Filed: Aug. 28, 2015

(65) Prior Publication Data

US 2016/0058538 A1  Mar. 3, 2016

Related U.S. Application Data

(60) Provisional application No. 62/043,635, filed on Aug. 29, 2014.

(51) Int. Cl.
*A61M 29/00* (2006.01)
*A61F 2/01* (2006.01)

(52) U.S. Cl.
CPC .......... *A61F 2/01* (2013.01); *A61F 2002/016* (2013.01); *A61F 2210/0014* (2013.01); *A61F 2230/0019* (2013.01)

(58) Field of Classification Search
CPC ....... A61F 2/01; A61F 2/013; A61F 2002/016
See application file for complete search history.

(56) References Cited

U.S. PATENT DOCUMENTS

| 4,494,531 | A | 1/1985 | Gianturco |
| 4,832,055 | A | 5/1989 | Palestrant |
| 4,994,077 | A | 2/1991 | Dobben |
| 5,607,465 | A | 3/1997 | Camilli |
| 6,200,336 | B1 | 3/2001 | Pavcnik et al. |
| 6,623,506 | B2 | 9/2003 | McGuckin, Jr. et al. |
| 7,128,759 | B2 | 10/2006 | Osborne et al. |
| 7,303,571 | B2 | 12/2007 | Makower et al. |
| 7,361,189 | B2 | 4/2008 | Case et al. |
| 7,569,071 | B2 | 8/2009 | Haverkost et al. |

(Continued)

FOREIGN PATENT DOCUMENTS

| WO | WO2009088957 | 7/2009 |
| WO | WO2010099209 | 9/2010 |

OTHER PUBLICATIONS

European Patent Office, Examination report dated Apr. 13, 2017 for European patent application No. 10706443.8.

(Continued)

*Primary Examiner* — Ashley Fishback
(74) *Attorney, Agent, or Firm* — Buchanan Van Tuinen LLC

(57) ABSTRACT

A low profile intraluminal filter includes first and second wire members that define arcuate paths having only a single sigmoidal curve. Connectors join the wire members to form an opening between the wire members. Each connecting member of a plurality of connecting members is connected to the first and second wire members and extends across the opening. The plurality of connecting members provides a plurality of open cells that permit passage of fluid flow through the opening when the filter is deployed within a body vessel.

19 Claims, 4 Drawing Sheets

(56) References Cited

U.S. PATENT DOCUMENTS

| | | |
|---|---|---|
| 8,109,990 B2 | 2/2012 | Paul et al. |
| 8,475,516 B2 | 7/2013 | Paul et al. |
| 8,652,197 B2 | 2/2014 | Paul et al. |
| 9,078,748 B2 | 6/2015 | Paul et al. |
| 2001/0039450 A1 | 11/2001 | Pavcnik et al. |
| 2005/0187614 A1 | 8/2005 | Agnew |
| 2006/0241675 A1 | 10/2006 | Johnson et al. |
| 2007/0112423 A1 | 5/2007 | Chu |
| 2008/0046071 A1 | 2/2008 | Pavcnik |
| 2008/0140110 A1 | 6/2008 | Spence |
| 2009/0234434 A1 | 9/2009 | Johnson et al. |
| 2010/0217381 A1 | 8/2010 | Paul et al. |
| 2012/0130476 A1 | 5/2012 | Paul et al. |
| 2013/0289709 A1 | 10/2013 | Paul et al. |
| 2014/0155987 A1 | 6/2014 | Paul et al. |
| 2014/0309631 A1 | 10/2014 | McLawhorn et al. |
| 2016/0074011 A1* | 3/2016 | Johnson .................. A61F 2/01 600/424 |

OTHER PUBLICATIONS

International Searching Authority, The International Search Report and Written Opinion of the International Searching Authority, dated May 20, 2010, for International Application No. PCT/US2010/025245.

Complete Prosecution History, U.S. Appl. No. 13/930,723, Compiled Feb. 6, 2014.

Complete Prosecution History, U.S. Pat. No. 8,475,516, Compiled Feb. 6, 2014.

Complete Prosecution History, U.S. Pat. No. 8,109,990, Compiled Feb. 6, 2014.

Volcano Corporation, "Crux: Vena Cava Filter," www.volcanocorp.com, Brochure, pp. 1-2, retrieved Aug. 26, 2014.

* cited by examiner

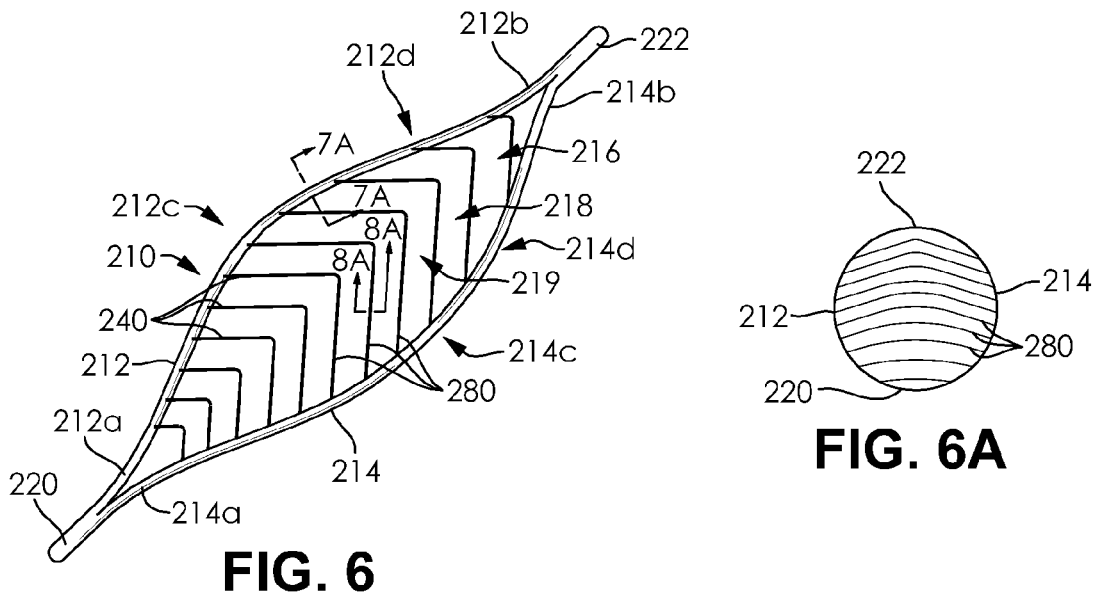
FIG. 6
FIG. 6A
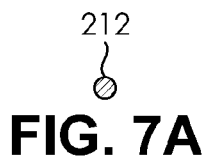
FIG. 7A
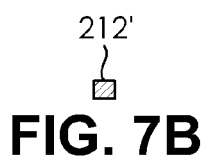
FIG. 7B
FIG. 7C
FIG. 8A
FIG. 8B
FIG. 8C
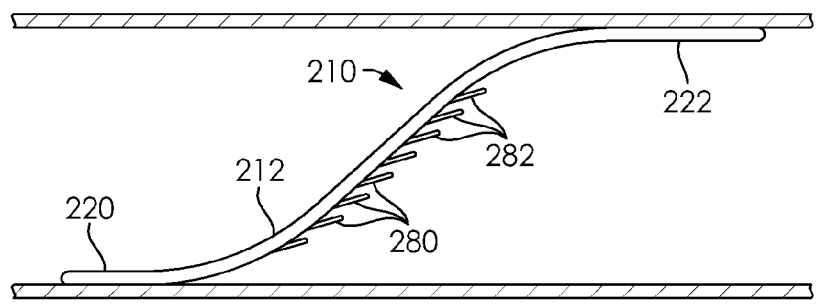
FIG. 9

LOW PROFILE INTRALUMINAL FILTERS

FIELD

The disclosure relates generally to the field of medical devices. More particularly, the disclosure relates to the field of medical devices suitable for use as intraluminal filters within body vessels, such as blood vessels.

BACKGROUND

A variety of expandable intraluminal medical devices have been developed over recent years. For example, stents are routinely used in several body lumens as a means for providing support to ailing vessels, such as coronary and non-coronary vessels. Occlusion devices are used to substantially block fluid flow through a body vessel, and prosthetic valves are used to regulate fluid flow through a body vessel. Both prosthetic heart valves and venous valves have been the subject of significant development efforts in recent years.

Expandable intraluminal medical devices are typically delivered to a point of treatment using a delivery system designed for percutaneous techniques. In a conventional procedure, a caregiver navigates the delivery system through one or more body vessels until the expandable intraluminal medical device, which is typically contained in a distal tip of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the intraluminal medical device in an expanded configuration at the point of treatment. This delivery and deployment technique is largely conventional and is used for most types of expandable intraluminal medical devices, including stents, occluders, valves, and other types of devices.

During delivery, expandable intraluminal medical devices are maintained in a compressed or reduced-diameter configuration within the delivery system to ensure navigability of the delivery system through the body vessel. The navigability of the delivery system is directly related to its overall outer diameter. A relatively large diameter limits the ability of a delivery system to be navigated past curves, angles, side branch openings and other impediments, and also limits the ability of a delivery system to enter and/or be navigated through small diameter vessels.

Because the delivery system must carry the intraluminal medical device to the point of treatment in the body vessel, efforts to minimize the outer diameter of delivery systems are necessarily confined by the ability of the intraluminal medical device to be compressed. The material, construction, and configuration of the medical device can limit its ability to be compressed, which, in turn, limits the useable outer diameter of the delivery system that will ultimately be used with the device.

Some intraluminal medical devices, including some prosthetic valves and occluders, include graft and/or valve members that add to the bulk of the support frame included in the device, compounding the difficulty associated with increasing the compressibility of the device. Intraluminal filters have presented a particular challenge in this regard as conventional approaches to enhancing the filtering function have tended to increase the overall bulk of these devices in an effort to increase the extent of the interaction between the filter and the fluid flowing through it. A need continues, therefore, for improved low profile medical devices in general and, in particular, for improved intraluminal filter devices.

BRIEF SUMMARY OF EXAMPLE EMBODIMENTS

Several example low profile intraluminal filters are described and illustrated herein. One example low profile intraluminal filter comprises a first wire member having first and second ends and defining a first arcuate path with a first curve disposed between the first and second ends, the first arcuate path comprising only a single sigmoidal curve; a second wire member having third and fourth ends and defining a second arcuate path with a second curve disposed between the third and fourth ends, the second arcuate path comprising only a single sigmoidal curve; a first connector connecting the first and third ends; a second connector connecting the second and fourth ends and spaced from the first connector on said lengthwise axis of said support frame, the first and second connectors connecting the first and second wire members to form an opening between the first and second wire members; and a plurality of connecting members extending across the opening from the first wire member to the second wire member, the plurality of connecting members and the first and second wire members cooperatively defining a plurality of open cells configured to permit passage of fluid flow through the opening when said low profile intraluminal filter is deployed within a body vessel.

Another example low profile intraluminal filter comprises a first wire member having first and second ends, a first thickness, and defining a first arcuate path with a first curve disposed between the first and second ends, the first arcuate path comprising only a single sigmoidal curve; a second wire member having third and fourth ends, a second thickness, and defining a second arcuate path with a second curve disposed between the third and fourth ends, the second arcuate path comprising only a single sigmoidal curve; a first connector connecting the first and third ends; a second connector connecting the second and fourth ends and spaced from the first connector on said lengthwise axis of said support frame, the first and second connectors connecting the first and second wire members to form an opening between the first and second wire members; and a plurality of connecting members attached to the first and second wire members and extending across the opening, each connecting member of the plurality of connecting members having a thickness that is less than the first and second thicknesses.

Another example low profile intraluminal filter comprises a first wire member having first and second ends, a first thickness, and defining a first arcuate path with a first curve disposed between the first and second ends, the first arcuate path comprising only a single sigmoidal curve; a second wire member having third and fourth ends, a second thickness, and defining a second arcuate path with a second curve disposed between the third and fourth ends, the second arcuate path comprising only a single sigmoidal curve; a first connector connecting the first and third ends; a second connector connecting the second and fourth ends and spaced from the first connector on said lengthwise axis of said support frame, the first and second connectors connecting the first and second wire members to form an opening between the first and second wire members; and a plurality of connecting members attached to the first and second wire members and extending across the opening, each connecting member of the plurality of connecting members having a thickness that is less than the first and second thicknesses and defining an apical bend.

Additional understanding of the claimed devices can be obtained by reviewing the description of example embodiments, below, with reference to the appended drawings.

BRIEF DESCRIPTION OF THE DRAWINGS

FIG. 6 is a perspective view of a third example filter.

FIG. 6A is an end view of the third example filter.

FIG. 7A is an enlarged sectional view of a wire member of the third example filter, taken along line 7A-7A in FIG. 6.

FIG. 7B is an enlarged sectional view of an alternative wire member.

FIG. 7C is an enlarged sectional view of an alternative wire member.

FIG. 8A is an enlarged sectional view of a connecting wire member of the third example filter, taken along line 8A-8A in FIG. 6.

FIG. 8B is an enlarged sectional view of an alternative connecting wire member.

FIG. 8C is an enlarged sectional view of an alternative connecting wire member.

FIG. 9 is a sectional view of a body vessel with the third example filter.

DETAILED DESCRIPTION OF EXAMPLE EMBODIMENTS

The following detailed description and appended drawings describe and illustrate various example embodiments of the invention. The description and drawings serve to enable one skilled in the art to make and use the inventive apparatuses; they are not intended to limit the scope of the invention or the protection sought in any manner.

As used herein, the term "plurality of connecting members" refers to a plurality of members that extend from a first wire member of a filter to a second wire member of the filter. The connecting members of a plurality of connecting members can comprise separate members that are structurally distinct from other connecting members of the plurality of connecting members other than being connected to the same first and second wire members of a filter. Alternatively, the connecting members of a plurality of connecting members can be integral with each other as components of a common structure containing all connecting members of the plurality of connecting members. For example, some or all of the connecting members of a plurality of connecting members may be serially connected to each other, such as in a thread. In these embodiments, each connecting member comprises a length of the thread that is less than the total length of the thread. In another example, some or all of the connecting members of a plurality of connecting members may comprise individual structural members in a sheet formed of a plurality of structural members that define a plurality of openings, such as a die-cut metal mesh.

Figure 1:
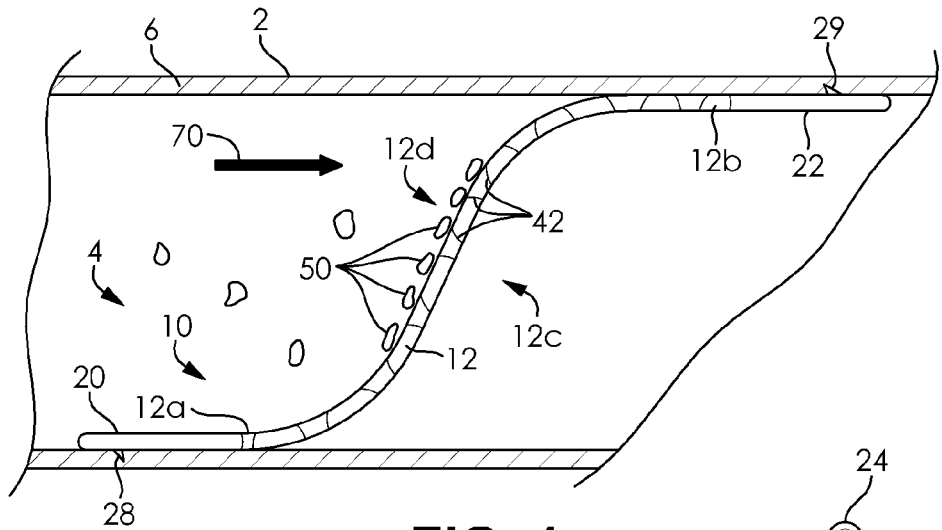
FIG. 1 is a sectional view of a body vessel with a first example filter.
Figure 2:
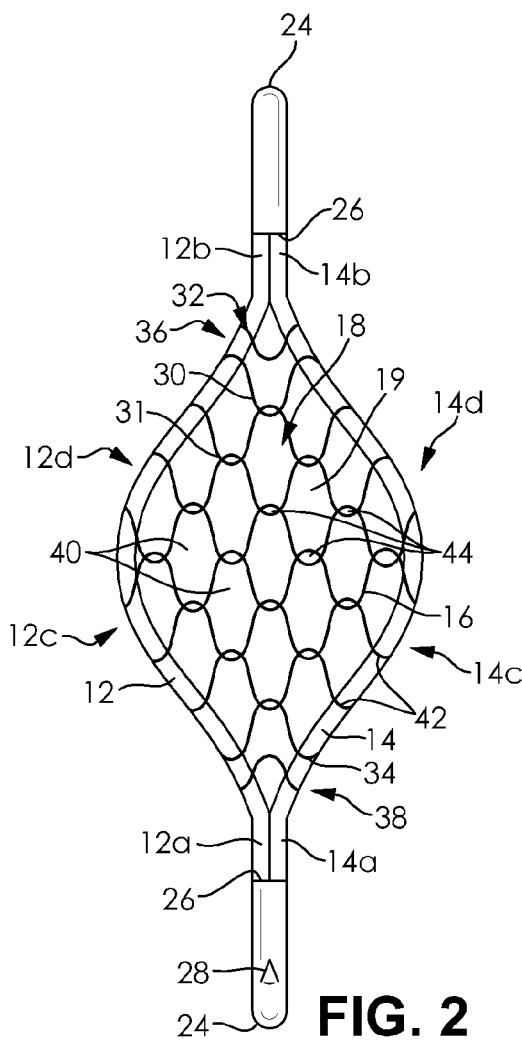
FIG. 2 is a top view of the first example filter in an expanded configuration.
Figure 3:
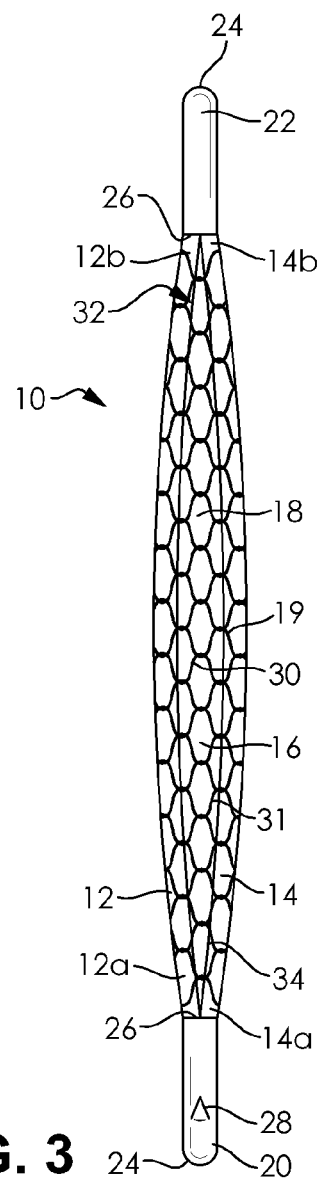
FIG. 3 is a top view of the first example filter in a non-expanded configuration.

FIGS. 1, 2 and 3 illustrate a first example filter 10. FIG. 1 illustrates the filter 10 disposed within the lumen 4 defined by a vessel wall 6 of a body vessel 2. FIGS. 1 and 2 illustrate the filter 10 in an expanded configuration; FIG. 3 illustrates the filter 10 in a non-expanded configuration.

The filter 10 includes first 12 and second 14 wire members and a plurality of connecting members 16 secured to the wire members 12, 14 and extending across a closed circumference 18 cooperatively defined by the wire members 12, 14. The plurality of connecting members 16 and the first 12 and second 14 wire members cooperatively define a plurality of open cells 40 that are configured to permit passage of fluid flow through the opening 19 defined by the closed circumference 18 when the low profile intraluminal filter 10 is deployed within a body vessel.

The first wire member 12 includes a first end 12a and a second end 12b. When the filter 10 is in the expanded configuration, the wire member 12 defines an arcuate path 12c with a curve 12d disposed between the first 12a and second 12b ends. The arcuate path and curve of the first wire member of a filter according to a particular embodiment can have any suitable size, shape and configuration. In the illustrated embodiment, the arcuate path 12c comprises only a single sigmoidal curve.

Similarly, the second wire member 14 includes first 14a and second 14b ends and, when the filter 10 is in the expanded configuration, defines an arcuate path 14c that includes a curve 14d disposed between the ends 14a, 14b. The arcuate path and curve of the second wire member of a filter according to a particular embodiment can have any suitable size, shape and configuration. In the illustrated embodiment, the arcuate path 14c has the same size, shape and configuration of the arcuate path 12c of the first wire member 12 and comprises only a single sigmoidal curve.

As best illustrated in FIG. 1, the wire members 12, 14 provide a minimal structure upon implantation of the filter 10 in the lumen 4 of a body vessel 2. Contrary to some trends in filter design, the low profile nature of the frame, provided by the wire members 12, 14 and connectors 20, 22, and the structure of the wire members 12, 14, described above, eliminates the need for additional structure for centering the filter 10 within the lumen 4. This elimination of bulk that would otherwise be contributed by a centering structure or other additional structure allows for inclusion of desired structure for the connecting members and the open cells that perform the filtering function.

The first 12 and second 14 wire members cooperatively define a closed circumference 18 that, in turn, defines opening 19. A first connector 20 is disposed at one end of the filter 10 and a second connector 22 is disposed at the opposite end of the filter 10. The first ends 12a, 14a of the first 12 and second wire 14 members are disposed within the first connector 20, and the second ends 12b, 14b of the first 12 and second 14 wire members are disposed in the second connector 22. Each of the connectors 20, 22 is attached to the appropriate ends 12a, 12b, 14a, 14b to maintain the closed circumference 18 defined by the wire members 12, 14. While the connectors 20, 22 are illustrated as hollow members that receive the ends 12a, 12b, 14a, 14b of the wire members 12, 14, it is understood that any suitable means for connecting wire members together can be used, including mechanical connections, such as crimping, adhesives, a connection formed by annealing or brazing, or any other suitable structure that provides a means for connecting wire members. Also, as noted below, one or both of the connectors 20, 22 can be integrally formed with one or both of the wire members 12, 14. The specific structure selected for the means for connecting the wire members in a support frame according to a particular embodiment of the invention will depend on various considerations, including the materials used in the wire members 12, 14.

The first 12 and second 14 wire members can have any suitable size, shape and configuration. Furthermore, the first 12 and second 14 wire members can have the same or different size, shape and configuration. In the embodiment illustrated in FIGS. 1, 2 and 3, the wire members 12, 14 each comprise a wire having a circular cross-sectional shape. Furthermore, the wire members 12, 14 have the same size, including the same length and diameter, and configuration. When the filter 10 is in its expanded configuration within a body vessel, such as the body vessel 2 illustrated in FIG. 1, the first 12 and second 14 wire members conform to the inner surface of the vessel wall.

Figure 4A:
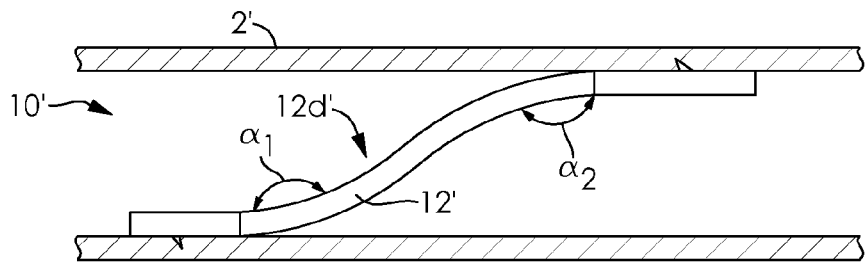
FIG. 4A is a sectional view of a body vessel with an alternative filter.
Figure 4B:
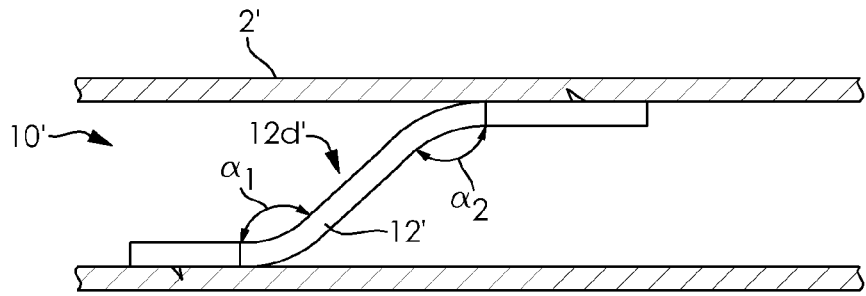
FIG. 4B is a sectional view of a body vessel with another alternative filter.
Figure 4C:
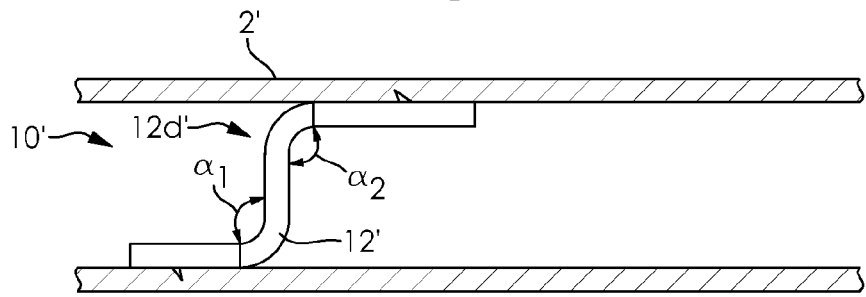
FIG. 4C is a sectional view of a body vessel with another alternative filter.

Each of FIGS. 4A, 4B, 4C illustrates an alternative filter 10' disposed within a body vessel 2'. In each of these figures, the first and second wire members of the illustrated filter have the same configurations. As a result, the second wire member is not visible in each figure. These figures illustrate the effect of different angles in the curve of the wire members, providing a range of examples of suitable configurations of one or more wire members in a filter according to an embodiment. FIG. 4A illustrates a first set of suitable inner angles $\alpha_1$, $\alpha_2$ of the curve 12d' of the first wire member 12'. FIG. 4B illustrates a first set of suitable inner angles $\alpha_1$, $\alpha_2$ of the curve 12d'. FIG. 4C illustrates a first set of suitable inner angles $\alpha_1$, $\alpha_2$ of the curve 12d'. Ranges of suitable angles for the inner angles of a curve defined by a wire member in a filter according to an embodiment when the filter is in an expanded configuration include an angle between about 90° and about 150, an angle between about 90° and about 135°, an angle between about 90° and about 120°, and an angle between about 90° and about 105°. As illustrated in FIGS. 4A, 4B and 4C, the inner angles can be selected to achieve a desired angle at which one or more wire members traverses the lumen of the body vessel when the filter is in an expanded configuration within the body vessel.

In the first example embodiment illustrated in FIGS. 1 through 3, the plurality of connecting members 16 comprises a mesh 31 formed from a single thread 30 having first 32 and second ends 34. The first end 32 is secured to the first wire member 12, such as by knot 36, and the second end 34 is secured to the second wire member 14, such as by knot 38. The ends 32, 34 can be secured to the wire members 12, 14 in any manner, and the illustrated knots 36, 38 are only examples. Other examples include adhesive(s) and mechanical connections to the wire members 12, 14.

As best illustrated in FIG. 2, the thread 30 is woven upon itself to form a plurality of open cells 40 within the opening 19 defined by the closed circumference 18 formed by the wire members 12, 14. The thread 30 is partially wrapped around the wire members 12, 14 at a plurality of locations 42. In several locations, the thread 30 passes through an open cell 40 and crosses itself to form an interface 44 where one portion of the thread 30 contacts another portion of the thread 30. In the illustrated Figures, each of the interfaces 44 is dynamic in that the thread portions are not secured to each other. This structural arrangement allows the open cells to change shape and or size as the wire members 12, 14 change structure, such as by going from an expanded configuration to a non-expanded configuration. Alternatively, at least one of, some of, or all of the interfaces 44 can be rendered static by securing the thread portions to each other, such as with an adhesive or by forming a knot. Inclusion of static interfaces may be desirable if a constant size and/or shape is desired for the some or all of the open cells 40.

The open cells of a filter according to a particular embodiment can have any suitable size, shape and configuration. A skilled artisan will be able to configure the wire members and connecting members of a filter according to a particular embodiment to achieve any desired size, shape and configuration for the open cells. Furthermore, a skilled artisan will be able to select a suitable size, shape and configuration for open cells in a filter according to a particular embodiment based on various considerations, including any size, shape and/or configuration of particulates desired to be filtered from fluid flow by the filter. Furthermore, all open cells in a filter according to a particular embodiment can have the same size, shape and/or configuration, or one or more open cells in a filter according to a particular embodiment can have a different size, shape and/or configuration than other open cells in the filter. Examples of suitable sizes for an inferior vena cava filter include open cells have an opening with a dimension of between 0.5 mm to 8 mm. Open cells having an opening with a dimension of between 1 mm and 6 mm are considered suitable for an inferior vena cava filter. Open cells having an opening with a dimension of between 2 mm and 5 mm are considered suitable for an inferior vena cava filter. Open cells having an opening with a dimension of between 3 mm and 4 mm are considered suitable for an inferior vena cava filter. Open cells having an opening with a dimension of about 1 mm are also considered suitable. Open cells having an opening with a dimension of about 2 mm are also considered suitable. Open cells having an opening with a dimension of about 3 mm are also considered suitable. Open cells having an opening with a dimension of about 4 mm are also considered suitable. Open cells having an opening with a dimension of about 5 mm are also considered suitable. Open cells having an opening with a dimension of about 6 mm are also considered suitable. Open cells having an opening with a dimension of about 7 mm are also considered suitable. Open cells having an opening with a dimension of about 8 mm are also considered suitable. Also, open cells having a generally circular shape are considered suitable. Examples of other suitable shapes include, circular, square, generally square, rectangular, generally rectangular, triangular, generally triangular, and other shapes.

The plurality of connecting members 16 can comprise any suitable structure that provides the plurality of open cells 40, and the mesh 31 formed from thread 30 in the example embodiment illustrated in FIGS. 1 through 3 is only an example. A pre-formed sheet having a plurality of open cells formed in it and that can be secured to the wire members 12, 14, such as with sutures or other suitable attachment structures, can also be used as a plurality of connecting members in a filter according to an embodiment. As such, the presence of interfaces at which a connecting member of the plurality of connecting members crosses itself, is optional.

The plurality of connecting members 16 can be formed of any suitable material, and a skilled artisan will be able to select an appropriate material for a filter according to a particular embodiment based on various considerations, such as any desired flexibility of the filter, the need or desired for dynamic or static interfaces, and manufacturing considerations. In the illustrated example embodiment, the thread 30 is a medical suture. Other examples of suitable materials include metal materials, including stainless steel filaments and die-cut stainless steel sheets, polymeric materials, such as polytetrafluoroethylene (PTFE), expanded PTFE (ePTFE) and other polymeric materials, and other materials considered suitable for use in implantable medical devices.

It is noted that, while the filter 10 is illustrated as being formed of independent wire members 12, 14 connected to each other, a filter or portion of a filter according to an embodiment can be formed of a unitary piece of material using suitable techniques and materials. For example, a filter can be cut from a tube of shape memory material using conventional or other suitable techniques. For example, a filter could be cut from a tube of nitinol using laser cutting or other suitable techniques, followed by expansion and heat treatment steps that are known in the art. In these unitary embodiments, the wire members comprise struts in the resulting structure and the connectors comprise joints at which individual struts are joined to each other. Connectors that are separate and distinct from the struts are not necessary in these embodiments—the joints perform the connecting function of the connectors in these embodiments. Also, a single wire member could be used to form a filter using suitable bending techniques. In these embodiments, bends in the wire member eliminate the need for connectors. It is noted, though, that in these embodiments, the inclusion of one or more connectors might still be considered advantageous as a crimping force providing by the connector may maintain a bend in the single wire member in a minimal thickness. It is also noted that a single wire member having one end formed by a bend and the other end formed by attaching two independent ends of the single wire member can be used to form the support frame.

In the illustrated embodiment, each connector 20, 22 includes a closed 24 and an open 26 end. The open end 26 is sized and configured to receive the appropriate ends 12a, 12b, 14a, 14b, 16a, 16b of the wire member 12, 14, 16. The closed end 24 does not provide access to the inside of the connector 20, 22. A barb is advantageously included on each of the connectors 20, 22. In this embodiment, the barb 28 on the first connector 20 is disposed on a surface of the first connector 20 that faces in a substantially opposite direction than the direction faced by the surface of the second connector 22 on which barb 29 is disposed, relative to a plane containing the closed circumference 16 defined by the wire members 12, 14. Also in this embodiment, the first barb 28 extends away from the first connector 20 in a direction that is different from the direction in which the second barb 29 extends away from the second connector 22. As best illustrated in FIG. 1, the barbs 28, 29 advantageously extend away from the respective connector 20, 22 in substantially opposite directions. This configuration is expected to provide advantageous anchoring characteristics for the medical device 10. It is noted that the barbs 28, 29 are not necessarily drawn to scale relative to any other component and/or element of the medical device 10, and are shown as relatively large elements for illustrative purposes only.

In use, filters according to embodiments are deployed into a lumen of a body vessel, such as a blood vessel. FIG. 1 illustrates the first example filter 10 disposed within lumen 4 of blood vessel 2. The plurality of connecting members 16, not visible in FIG. 1, blocks passage of particulates 50 that are too large to pass through an open cell 40 defined by the plurality of connecting members 16 as fluid flow, represented by arrow 70, passes through the opening 19 formed by the closed circumference 18 defined by the first 12 and second 14 wire members. Filters according to particular embodiments can be used in any body vessel in which it is desired to capture particulates or other material contained within fluid flowing through the body vessel. For example, filters according to the embodiments described herein are suitable for use inferior vena cava filters that are implanted into the inferior vena cava using minimally invasive introduction and deployment techniques.

Figure 5:
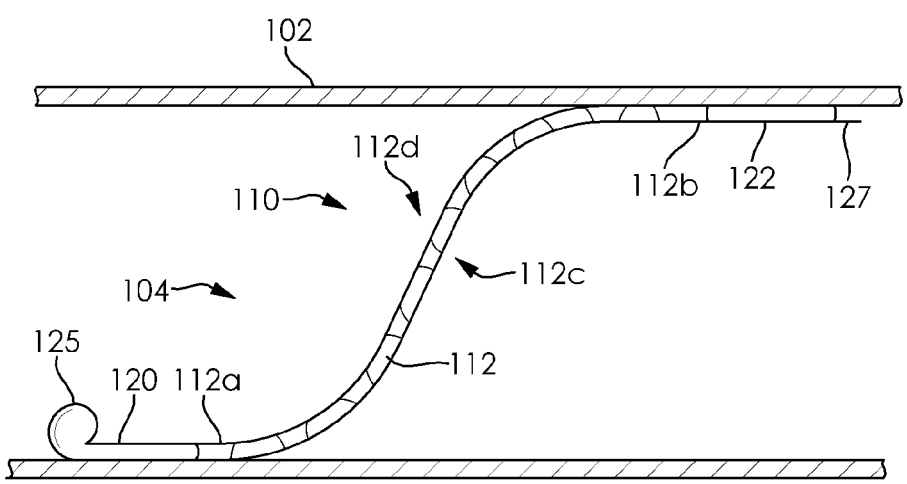
FIG. 5 is a sectional view of a body vessel with a second example filter.

Filters according to particular embodiments can include additional structural features. For example, FIG. 5 illustrates another example filter 110 that includes structural features that enable retrieval of the filter 110 from a location within the lumen 104 of a body vessel 102. The filter 110 is similar to the filter 10 illustrated in FIGS. 1 through 3 and described above, except as indicated below. Thus, the filter 110 includes first 112 and second (not visible in FIG. 5) wire members and a plurality of connecting members (not visible in FIG. 5). The first wire member 112 includes a first end 112a and a second end 112b. When the filter 110 is in the expanded configuration, the wire member 112 defines an arcuate path 112c with a curve 112d disposed between the first 112a and second 112b ends. The arcuate path 112c comprises only a single sigmoidal curve. The second wire member includes first and second ends and, when the filter 110 is in the expanded configuration, defines an arcuate path that includes a curve disposed between the ends. The arcuate path has the same size, shape and configuration of the arcuate path 112c of the first wire member 112 and comprises only a single sigmoidal curve. A first connector 120 is disposed at one end of the filter 110 and a second connector 122 is disposed at the opposite end of the filter 110. The first ends 112a, 114a of the first 112 and second wire members are disposed within the first connector 120, and the second ends 112b, 114b of the first 112 and second wire members are disposed in the second connector 122. Each of the connectors 120, 122 is attached to the appropriate ends 112a, 112b to maintain the closed circumference defined by the wire members.

In this embodiment, the first connector 120 provides an inwardly-directed projection 125 on its end. The inwardly-directed projection 125 has a rounded or ball shape. Any suitable structure can be included to facilitate retrieval. For example, in the illustrated embodiment, the second connector 122 provides a tab member that defines a loop 127, which is also considered suitable. Each of these structures, and others with suitable shapes and configurations, can be used to engage the filter with a suitable retrieval device capable of grasping the inwardly-directed projection 125, 127, such as a snare, grasper, or other suitable retrieval device. Furthermore, while the illustrated filter 110 includes two structures 125, 127 for facilitating retrieval, a filter according to a particular embodiment can have only a single structure disposed on one of the connectors 120, 122.

FIGS. 6, 6A, 7A, 8A and 9 illustrate another example filter 210. The filter 210 is similar to the filter 10 illustrated in FIGS. 1 through 3 and described above, except as indicated below. Thus, the filter 210 includes first 212 and second 214 wire members that define a closed circumference 218. The first wire member 212 includes a first end 212a and a second end 212b. When the medical device 210 is in the expanded configuration, the wire member 212 defines an arcuate path 212c with a curve 212d disposed between the first 212a and second 212b ends. The arcuate path 212c comprises only a single sigmoidal curve. The second wire member 214 includes first 214a and second 214b ends and, when the filter 210 is in the expanded configuration, defines an arcuate path 214c that includes a curve 214d disposed between the ends. The arcuate path 214c has the same size, shape and configuration of the arcuate path 212c of the first wire member 212 and comprises only a single sigmoidal curve. A first connector 220 is disposed at one end of the filter 210 and a second connector 222 is disposed at the opposite end of the filter 210. In this embodiment, the filter 210 is formed as a unitary device cut from a section of a tube, such as a tube of nickel titanium alloy. As such, both wire members 212, 214 and both connectors 220, 222 are integral with each other. The first ends 212a, 214a of the first 212 and second 214 wire members converge and join each other to form the first connector 220, and the second ends 212b, 214b of the first 212 and second 214 wire members converge and join each other to form the second connector 222.

In all embodiments, all wire members can have any suitable configuration. For example, the wire members can be formed from one or more lengths of wire or can be cut from a solid tubular section of material. Furthermore, the wire members can have any suitable cross-sectional shape. As best illustrated in FIG. 7A, the wire member 212, indeed all wire members in the illustrated embodiment, have a generally circular cross-sectional shape. Other examples of suitable cross sectional shapes include a generally square cross sectional shape, such as the alternative wire member 212' illustrated in FIG. 7B, a generally D-shaped cross-section shape, such as the alternative wire member 212" illustrated in FIG. 7C, a generally triangular cross-sectional shape, a generally ovoid cross-sectional shape, and a generally rectangular cross-sectional shape.

In this embodiment, connecting members 280 of a plurality of connecting members 216 are individually attached to the first 212 and second 214 wire members and extend across the opening 219 formed by the closed circumference 218 defined by the first 212 and second 214 wire members. Thus, in this embodiment, the plurality of connecting members 216 comprises a group of individual connecting members 280 that are structurally distinct from other connecting members 280 of the plurality of connecting members 216 other than being connected to the same first 212 and second 214 wire members of filter 210. In this embodiment, none of the individual connecting members 280 of the plurality of connecting members 216 interface with another connecting member 280, and each open cell of the plurality of open cells 240 is cooperatively defined by two connecting members 280 of the plurality of connecting members 280 and the first 212 and second 214 wire members.

Any suitable size, shape, configuration and number of connecting members can be used in a filter according to a particular embodiment. A skilled artisan will be able to determine an appropriate size, shape, configuration and number of connecting members for a filter according to a particular embodiment based on various considerations, including any desired flexibility and/or profile of the filter and any desired size, shape and/or configuration for one or more open cells of the filter. In the illustrated embodiment, each connecting member 280 comprises a wire member with an apical bend 282 disposed approximately midway between the first 212 and second 214 wire members. This particular structural arrangement is of interest because it provides a stacking arrangement to the connecting members 280 when the filter is deployed within a body vessel, as best illustrated in FIGS. 6A and 9. This arrangement is considered advantageous at least because it increases the spatial distribution of the filtering structure without comprising the low profile nature of the overall filter 210. As best illustrated in FIG. 8A, each connecting member 280 has a generally circular cross-sectional shape and has a diameter that is less than the diameter of the wire members 212, 214. Other examples of suitable cross sectional shapes for the connecting members 280 include a generally square cross sectional shape, such as the alternative wire member 280' illustrated in FIG. 8B, a generally D-shaped cross-sectional shape, such as the alternative connecting member 280" illustrated in FIG. 8C, a generally triangular cross-sectional shape, a generally ovoid cross-sectional shape, and a generally rectangular cross-sectional shape.

Any suitable axial spacing between connecting members in a filter according to a particular embodiment can be used. In the illustrated embodiment, connecting members 280 are spaced approximately equidistantly from each other along the lengthwise axis of the filter 210. Irregular and/or non-uniform axial spacings can also be used.

Figure 10:
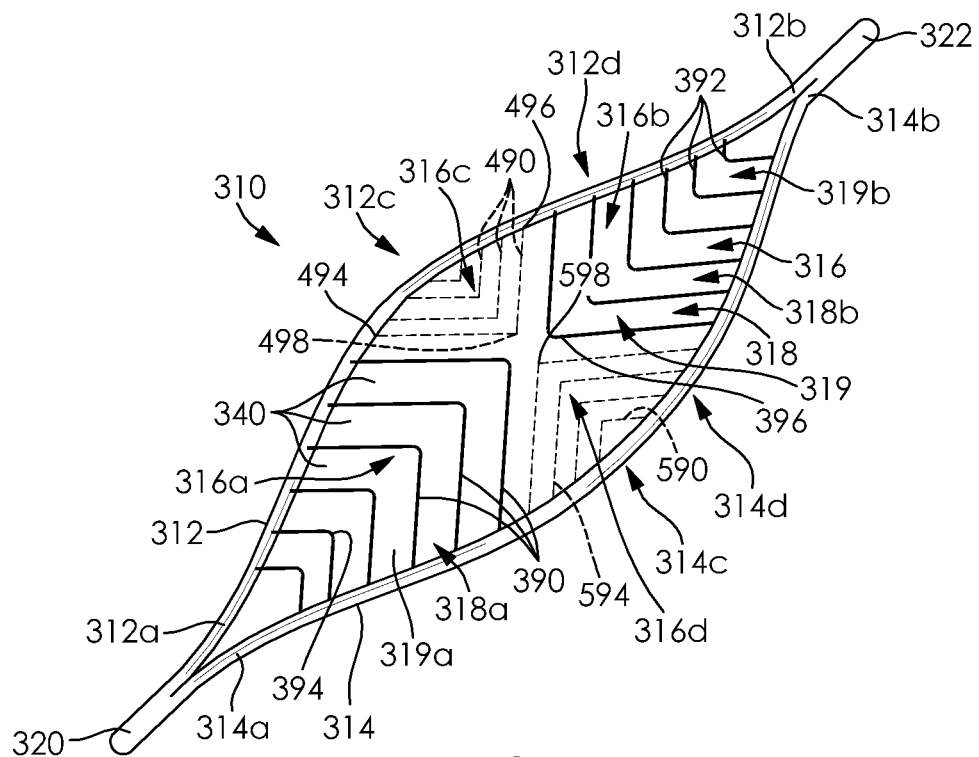
FIG. 10 is a perspective view of a fourth example filter.
Figure 10A:
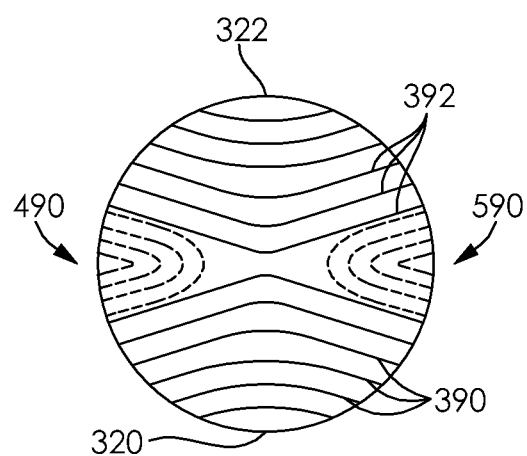
FIG. 10A is an end view of the fourth example filter.

FIGS. 10 and 10A illustrate another example filter 310. The filter 310 is similar to the filter 210 illustrated in FIGS. 6, 6A, 7A, 8A, and 9, except as indicated below. Thus, the filter 310 includes first 312 and second 314 wire members that define a closed circumference 318. The first wire member 312 includes a first end 312a and a second end 312b. When the medical device 310 is in the expanded configuration, the wire member 312 defines an arcuate path 312c with a curve 312d disposed between the first 312a and second 312b ends. The arcuate path 312c comprises only a single sigmoidal curve. The second wire member 314 includes first 314a and second 314b ends and, when the filter 310 is in the expanded configuration, defines an arcuate path 314c that includes a curve 314d disposed between the ends. The arcuate path 314c has the same size, shape and configuration of the arcuate path 312c of the first wire member 312 and comprises only a single sigmoidal curve. A first connector 320 is disposed at one end of the filter 310 and a second connector 322 is disposed at the opposite end of the filter 310. In this embodiment, the filter 310 is formed as a unitary device cut from a section of a tube, such as a tube of nickel titanium alloy. As such, both wire members 312, 314 and both connectors 320, 322 are integral with each other. The first ends 312a, 314a of the first 312 and second 314 wire members converge and join each other to form the first connector 320, and the second ends 312b, 314b of the first 312 and second 314 wire members converge and join each other to form the second connector 322.

In this embodiment, connecting members 390 of a first series of connecting members 316a are disposed in a first portion 319a of the opening 319 formed by the closed circumference 318 defined by the first 312 and second 314 wire members. Each connecting member 390 of the first series of connecting members 316a is individually attached to the first 312 and second 314 wire members and extends across the first portion 319a of the opening 319 formed by the closed circumference 318. Connecting members 392 of a second series of connecting members 316b are disposed in a first portion 319b of the opening 319 formed by the closed circumference 318 defined by the first 312 and second 314 wire members. Each connecting member 392 of the second series of connecting members 316b is individually attached to the first 312 and second 314 wire members and extends across the second portion 319b of the opening formed by closed circumference 318. Thus, in this embodiment, the plurality of connecting members 316 comprises the first 316a and second 316b series of connecting members. In this embodiment, none of the individual connecting members 390, 392 of the series of connecting members 316a, 316b interface with another connecting member 390, 392, and each open cell of the plurality of open cells 340 is cooperatively defined by two individual connecting members 390 of the first series of connecting members 316a, two individual connecting members 392 of the second series of connecting members 316b, or an individual connecting member 390 of the first series of connecting member 316a and an individual connecting member 316b of the second series of connecting members 316b, and the first 312 and second 314 wire members.

In this embodiment, each connecting member 390 of the first series of connecting members 316a comprises a wire member with an apical bend 394 disposed approximately midway between the first 312 and second 314 wire members. Similarly, each connecting member 392 of the second series of connecting members 316b comprises a wire member with an apical bend 396 disposed approximately midway between the first 312 and second 314 wire members. The series 390, 392 of connecting members are oriented in opposing directions such that, from its apical bend 394, each connecting member 390 of the first series of connecting members 316a extends away from each connecting member 392 of the second series of connecting members 316b and such that, from its apical bend 396, each connecting member 392 of the second series of connecting members 316b extends away from each connecting member 390 of the first series of connecting members 316a.

As best illustrated in FIG. 10, optional third 316c and fourth 316d series of connecting members can be included in a filter according to a particular embodiment. In the illustrated embodiment, each connecting member 490 of the third series of connecting members 316c comprises a wire member that is connected to the first wire member 312 at two distinct points. Each connecting member 490 of the third series of connecting members 316c extends into the opening 319 formed by the closed circumference 318 from first 494 and second 496 points of attachment with the first wire member 312 and includes an apical bend 498. Similarly, each connecting member 590 of the fourth series of connecting member 316d comprises a wire member that is connected to the second wire member 312 at two distinct points. Each connecting member 590 of the fourth series of connecting members 316d extends into the opening 319 formed by the closed circumference 318 from first 594 and second 596 points of attachment with the first wire member 312 and includes an apical bend 598. This arrangement is considered advantageous at least because it increases the spatial distribution of the filtering structure and forms a tortuous path for fluid flowing through the filter 310 without compromising the low profile nature of the overall filter 310.

The plurality of connecting members in a filter according to a particular embodiment can comprise a combination of different types of pluralities of connecting members, such as those described herein. For example, a plurality of connecting members that comprises one or more series of connecting members, such as the plurality of connecting member 216 of the filter 210 illustrated in FIGS. 6, 6A, 7A, 8A and 9 and the plurality of connecting members 316 of the filter 310 illustrated in FIGS. 10 and 11, can be combined with a mesh formed of one or more thread members, such as the mesh 31 of the filter 10 illustrated in FIGS. 1 through 3, and/or a sheet having pre-defined open cells. Indeed, any suitable combination of pluralities of connecting members can be used in a filter according to a particular embodiment, and a skilled artisan will be able to select an appropriate overall structure based on various considerations, including any specific filtration needs or concerns at a particular point of treatment at which the filter is intended to be used.

In all embodiments, the wire members can be formed of any suitable resilient material acceptable for use in implantable medical devices. Examples of suitable materials include, but are not limited to, stainless steel, nitinol, nickel-cobalt-chromium alloys, nickel-cobalt-chromium-molybdenum alloys, polymeric materials, and other biocompatible materials. Nickel-cobalt-chromium-molybdenum alloys, such as MP35N (Carpenter Technology, Wyomissing, Pa.; MP35N is a registered trademark of SPS Technologies, Inc.), are considered particularly advantageous at least because of the relatively high tensile strength provided by these materials. As used herein, the term "wire member" does not refer to any particular size, diameter, or cross-sectional shape. While wire members having substantially circular cross-sectional shapes offer particular advantages, they are not required. Examples of other suitable cross-sectional shapes include, but are not limited to, flat, square, triangular, D-shaped, trapezoidal, and delta-shaped cross-sectional shapes. Also, as mentioned above, a medical device according to an embodiment can comprise a unitary member cut from an appropriate material, such as from a tube of shape memory material. In these embodiments, the wire members comprise struts in the structure resulting from the cutting process.

Also, the connectors in all embodiments can be formed from the same material or a different material than that of the wire members. Skilled artisans will be able to select appropriate materials for use in a support frame according to a particular embodiment of the invention based on various considerations, including the intended use, treatment environment and manufacturing demands of the medical device. The inventors have determined that wire members formed of nitinol and connectors formed of stainless steel provide a medical device with desirable characteristics for use in a variety of applications, including as a component in intraluminal medical devices, such as stents, prosthetic valves, and occluders.

While the medical devices described herein are considered useful independent of additional components, other components and or functionalities can be added to the various structures described herein to provide new and useful intraluminal medical devices of various types.

While various embodiments are described with reference to specific features of particular drawings, it is understood that the various elements and/or features described herein in connection with one particular embodiment can be combined with those of another without departing from the scope of the invention. Furthermore, the embodiments described and illustrated herein represent examples selected by the inventors for the purpose of describing the invention; they are not intended to limit the scope of the invention in any manner. Rather, they serve only to aid those skilled in the art to make and use the invention.

We claim:
1. A low profile intraluminal filter having a lengthwise axis, a radially compressed configuration and a radially expanded configuration, said low profile intraluminal filter comprising:
   a first wire member having first and second ends and defining a first arcuate path with a first curve disposed between the first and second ends, the first arcuate path comprising only a single sigmoidal curve;
   a second wire member having third and fourth ends and defining a second arcuate path with a second curve disposed between the third and fourth ends, the second arcuate path comprising only a single sigmoidal curve;

a first connector connecting the first and third ends;

a second connector connecting the second and fourth ends and spaced from the first connector on said lengthwise axis of said support frame, the first and second connectors connecting the first and second wire members to form an opening between the first and second wire members; and a plurality of connecting members extending across the opening from the first wire member to the second wire member, the plurality of connecting members and the first and second wire members cooperatively defining a plurality of open cells configured to permit passage of fluid flow through the opening when said low profile intraluminal filter is deployed within a body vessel.

2. The low profile intraluminal filter of claim 1, wherein the first connector comprises a separate member attached to the first and third ends.

3. The low profile intraluminal filter of claim 1, wherein the second connector comprises a separate member attached to the second and fourth ends.

4. The low profile intraluminal filter of claim 1, wherein the first curve is disposed substantially opposite the second curve.

5. The low profile intraluminal filter of claim 1, wherein the first and second wire members are formed of nitinol.

6. The low profile intraluminal filter of claim 1, wherein the first and second wire members are formed of stainless steel.

7. The low profile intraluminal filter of claim 1, wherein the plurality of connecting members comprises a mesh.

8. The low profile intraluminal filter of claim 7, wherein the mesh comprises a thread.

9. The low profile intraluminal filter of claim 8, wherein the thread has first and second ends; and wherein the first end is secure to the first wire member and the second end is secured to the second wire member.

10. The low profile intraluminal filter of claim 1, wherein the plurality of connecting members comprises a first series of connecting members, each connecting member of the first series of connecting members attached to the first and second wire members and extending across the opening to cooperatively define an open cell of the plurality of open cells with the first and second wire members and another connecting member of the plurality of connecting members.

11. The low profile filter of claim 10, wherein each connecting member of the first series of connecting members defines an apical bend.

12. The low profile filter of claim 10, wherein the plurality of connecting members further comprises a second series of connecting members, each connecting member of the second series of connecting members attached to the first and second wire members and extending across the opening to cooperatively define an open cell of the plurality of open cells with the first and second wire members and another connecting member of the plurality of connecting members;

wherein the each connecting member of the second series of connecting members defines an apical bend;

wherein, each connecting member of the first series of connecting members extends away from each connecting member of the second series of connecting members from its apical bend; and wherein each connecting member of the second series of connecting members extends away from each connecting member of the first series of connecting members from its apical bend.

13. The low profile filter of claim 12, wherein the plurality of connecting members further comprises a third series of connecting members;

wherein each connecting member of the third series of connecting members is attached to the first wire member at first and second locations; and wherein each connecting member of the third series of connecting members defines an apical bend.

14. A low profile intraluminal filter having a lengthwise axis, a radially compressed configuration and a radially expanded configuration, said low profile intraluminal filter comprising:

a first wire member having first and second ends and defining a first arcuate path with a first curve disposed between the first and second ends, the first arcuate path comprising only a single sigmoidal curve;

a second wire member having third and fourth ends and defining a second arcuate path with a second curve disposed between the third and fourth ends, the second arcuate path comprising only a single sigmoidal curve;

a first connector connecting the first and third ends;

a second connector connecting the second and fourth ends and spaced from the first connector on said lengthwise axis of said support frame, the first and second connectors connecting the first and second wire members to form an opening between the first and second wire members; and a plurality of connecting members extending across the opening from the first wire member to the second wire member, the plurality of connecting members and the first and second wire members cooperatively defining a plurality of open cells configured to permit passage of fluid flow through the opening when said low profile intraluminal filter is deployed within a body vessel;

wherein the plurality of connecting members comprises a mesh;

wherein the mesh comprises a thread; and wherein the thread is woven upon itself to define some of the plurality of open cells.

15. The low profile intraluminal filter of claim 14, wherein the thread forms a plurality of interfaces; and wherein a first portion of the thread contacts a second portion of the thread at each interface.

16. The low profile intraluminal filter of claim 15, wherein each of the interfaces is dynamic.

17. The low profile intraluminal filter of claim 15, wherein at least one of the interfaces is static.

18. The low profile intraluminal filter of claim 15, wherein all of the interfaces are static.

19. A low profile intraluminal filter having a lengthwise axis, a radially compressed configuration and a radially expanded configuration, said low profile intraluminal filter comprising:

a first wire member having first and second ends, a first thickness, and defining a first arcuate path with a first curve disposed between the first and second ends, the first arcuate path comprising only a single sigmoidal curve;

a second wire member having third and fourth ends, a second thickness, and defining a second arcuate path with a second curve disposed between the third and fourth ends, the second arcuate path comprising only a single sigmoidal curve;

a first connector connecting the first and third ends;

a second connector connecting the second and fourth ends and spaced from the first connector on said lengthwise axis of said support frame, the first and second connectors connecting the first and second wire members to form an opening between the first and second wire members; and a plurality of connecting members attached to the first and second wire members and extending across the opening, each connecting member of the plurality of connecting members having a thickness that is less than the first and second thicknesses.

* * * * *